(12) United States Patent
Ji et al.

(10) Patent No.: US 9,795,134 B2
(45) Date of Patent: Oct. 24, 2017

(54) GROWTH ENHANCEMENT OF PLANT

(71) Applicant: RHODIA OPERATIONS, Paris (FR)

(72) Inventors: PengFei Ji, Shanghai (CN); Galder Cristobal, Singapore (SG)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/413,070

(22) PCT Filed: Jul. 8, 2013

(86) PCT No.: PCT/CN2013/078982
§ 371 (c)(1),
(2) Date: Jan. 6, 2015

(87) PCT Pub. No.: WO2014/005555
PCT Pub. Date: Jan. 9, 2014

(65) Prior Publication Data
US 2015/0157015 A1  Jun. 11, 2015

(30) Foreign Application Priority Data
Jul. 6, 2012 (WO) ................ PCT/CN2012/078274

(51) Int. Cl.
*A01N 25/00* (2006.01)
*A01N 43/16* (2006.01)
*A01C 1/06* (2006.01)
*A01N 43/653* (2006.01)

(52) U.S. Cl.
CPC ................ *A01N 43/16* (2013.01); *A01C 1/06* (2013.01); *A01N 43/653* (2013.01)

(58) Field of Classification Search
None
See application file for complete search history.

(56) References Cited

U.S. PATENT DOCUMENTS 9,096,793 B2 * 8/2015 Cristobal ............... C09K 17/52
2005/0256001 A1   11/2005 Smith et al.
2012/0220454 A1   8/2012 Chen et al.

FOREIGN PATENT DOCUMENTS

| CN | 102115503 A | 7/2011 |
| CN | 102515959 A | 6/2012 |
| WO | 2004/071195 A1 | 8/2004 |
| WO | 2012/118795 A2 | 9/2012 |

* cited by examiner

*Primary Examiner* — Alton Pryor
(74) *Attorney, Agent, or Firm* — Jarrod N. Raphael

(57) ABSTRACT

The present invention concerns a method to increase the growth of a plant by coating a seed of said plant with a composition comprising at least a cationic guar; notably permitting to develop its biomass and reach its maturity. The invention also concerns a seed coating composition used in such a method.

17 Claims, No Drawings

GROWTH ENHANCEMENT OF PLANT

This application is a U.S. national phase entry under 35 U.S.C. §371 of International Application No. PCT/CN2013/078982, filed on Jul. 8, 2013, which claims the priority of International Application No. PCT/CN2012/078274, filed on Jul. 6, 2012. The entire contents of these applications are being incorporated herein by reference for all purposes.

The present invention concerns a method to increase the growth of a plant by coating a seed of said plant with a composition comprising at least a cationic guar; notably permitting to develop its biomass and reach its maturity. The invention also concerns a seed coating composition used in such a method.

Economic demands, environmental concerns, and ecological considerations require that farmers continually improve their agricultural practices. These economic demands require that farmers utilize the most cost efficient practices in order to generate the highest crop yields, while using fewer chemicals with lower toxicity as environmental considerations. Finally, ecological considerations have led to integrated pest management systems which further challenge the farmer's ability to produce crop yields and quality within the economic constraints prevalent in today's market.

Plant, soil and seed treatments are used on almost every commercial crop on the market today. In this era of intensified agriculture, the seed is modified to obtain higher crop yields and high quality.

As example, WO patent application WO2004071195 discloses a method to increase crop yield and accelerating crop emergence comprising administering a composition including a polysaccharide on a seed or seed piece of said crop or to a soil in which said crop is cultivated. U.S. Pat. No. 5,554,445 describes a seed encrusting method by use of microcrystalline chitosan in a form of liquid dispersion to form a highly adhesive, permeable, biodegradable and bioactive film on the seed surface. The seed encrusting preparation consists of providing a uniform coating of the seed with a mixture of seed, encrusting agent and/or dyes and/or nutrient media that the preparation is optionally combined with. However the germination power mentioned in this prior art is clearly not sufficient as the number of sprouted plants may be increased but without a significant improvement of growth.

There is a need then to carry out a method to improve the germination rate and the crop yield but also the enhancement of growth of the obtained plant, notably permitting to develop and increase its biomass.

It appear that now it's possible to set a seed treatment permitting to increase the enhancement of growth of a plant, notably permitting to develop its biomass and reach its maturity; that could not be obtained by the seed treatments involved in the prior art. The seed treatment also permits to increase the number of pods, the weight of grains and size, the length of roots and the general yield of produced plants, even in conditions wherein irrigation is insufficient.

The present invention concerns then a method to increase the growth of a plant which comprises at least a step to coat a seed of said plant with a composition comprising at least a cationic guar. The invention also concerns a method to increase the growth of a plant comprising administering a composition comprising at least a cationic guar on a seed of said plant.

In a first embodiment, the invention also concerns a method to increase the growth of a plant by coating a seed of said plant with a composition comprising at least a cationic guar in a first step and then in a second step to apply the coated seed onto or in the soil; notably in order to set in contact the coated seed with the ground. In an other embodiment, the invention also concerns a method to increase the growth of a plant in which it's perfectly possible to set an "in situ coating" onto or in the soil; notably by implanting in a hole in the soil a raw or non-coated seed of plant and then applying a coating composition comprising at least a cationic guar, into the hole to surround or partially surround the seed. The invention also concerns then a method to increase the growth of a plant comprising administering a composition comprising at least a cationic guar to a soil in which said crop is cultivated.

It is also an object of this invention to provide a method, which is easily carried out and easily applied using conventional and commercially available application equipment.

The method of the present invention involving a cationic guar also permits to decrease the detrimental effect of fungicide and herbicides that impact negatively germination rate and growth of plants.

Plants according to the present invention may be agricultural and horticultural plants, shrubs, trees and grasses, hereinafter sometimes collectively referred to as plants.

Seed is of the crop or plant species including but not limited to corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, woody plants such as conifers and deciduous trees, squash, pumpkin, hemp, zucchini, apple, pear, quince, melon, plum, cherry, peach, nectarine, apricot, strawberry, grape, raspberry, blackberry, soybean, sorghum, sugarcane, rapeseed, clover, carrot, and *Arabidopsis thaliana*.

In one embodiment, the seed is of any vegetables species including but not limited to tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), cauliflower, broccoli, turnip, radish, spinach, asparagus, onion, garlic, pepper, celery, and members of the genus *Cucumis* such as cucumber (*C. sativus*), cantaloupe (*C. cantalupensis*), and musk melon (*C. melo*).

In one embodiment, the seed is of any ornamentals species including but not limited to hydrangea (*Macrophylla hydrangea*), hibiscus (*Hibiscus rosasanensis*), petunias (*Petunia hybrida*), roses (*Rosa* spp.), azalea (*Rhododendron* spp.), tulips (*Tulipa* spp.), daffodils (*Narcissus* spp.), carnation (*Dianthus caryophyllus*), poinsettia (*Euphorbia pulcherrima*), and chrysanthemum.

In one embodiment, the seed is of any conifer species including but not limited to conifers pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

In one embodiment, the seed is of any leguminous plant species including but not limited beans and peas. Beans include guar, locust bean, fenugreek, soybean, garden beans, cowpea, mungbean, lima bean, fava bean, lentils, chickpea, pea, moth bean, broad bean, kidney bean, lentil, dry bean, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Typical forage and turf grass for use in the methods described herein include but are not limited to alfalfa, orchard grass, tall fescue, perennial ryegrass, creeping bent grass, lucerne, birdsfoot trefoil, clover, stylosanthes species, lotononis bainessii, sainfoin and redtop. Other grass species include barley, wheat, oat, rye, orchard grass, guinea grass, *sorghum* or turf grass plant.

In another embodiment, the seed is selected from the following crops or vegetables: corn, wheat, *sorghum*, soybean, tomato, cauliflower, radish, cabbage, canola, lettuce, rye grass, grass, rice, cotton, sunflower and the like.

It is understood that the term "seed" or "seedling" is not limited to a specific or particular type of species or seed. The term "seed" or "seedling" can refer to seed from a single plant species, a mixture of seed from multiple plant species, or a seed blend from various strains within a plant species. In one embodiment, crop seeds include but are not limited to rice, corn, wheat, barley, oats, soybean, cotton, sunflower, alfalfa, *sorghum*, rapeseed, sugarbeet, tomato, bean, carrot, tobacco or flower seeds.

The composition of the present invention may comprise one or more cationic guar. Cationic guars of the invention may include cationic guars that may be obtained by the use of different possible cationic etherifying agents, such as for example the family of quaternary ammonium salts.

In the case of cationic guars, the cationic group may be then a quaternary ammonium group bearing three radicals, which may be identical or different, chosen from hydrogen, an alkyl radical containing 1 to 22 carbon atoms, more particularly 1 to 14 and advantageously 1 to 3 carbon atoms. The counterion is generally a halogen, which is one embodiment is chlorine.

Quaternary ammonium salts may be for example: 3-chloro-2-hydroxypropyl trimethyl ammonium chloride (CHPTMAC), 2,3-epoxypropyl trimethyl ammonium chloride (EPTAC), and diallyldimethyl ammonium chloride (DMDAAC).

A typical cationic functional group in these cationic guar derivatives is trimethylamino(2-hydroxyl)propyl, with a counter ion. Various counter ions can be utilized, including but not limited to halides, such as chloride, fluoride, bromide, and iodide, sulfate, methylsulfate, and mixtures thereof.

Cationic guars of the present invention may be chosen in the group consisting of:
  cationic hydroxyalkyl guars, such as cationic hydroxyethyl guar (HE guar), cationic hydroxypropyl guar (HP guar), cationic hydroxybutyl guar (HB guar), and
  cationic carboxylalkyl guars including cationic carboxymethyl guar (CM guar), cationic alkylcarboxy guars such as cationic carboxylpropyl guar (CP guar) and cationic carboxybutyl guar (CB guar), carboxymethylhydroxypropyl guar (CMHP guar).

More preferably, cationic guars of the invention are guars hydroxypropyltrimonium chloride.

The degree of hydroxyalkylation (molar substitution or MS) of cationic guars, that is the number of alkylene oxide molecules consumed by the number of free hydroxyl functions present on the guar, may be comprised between 0 and 3, preferably between 0 and 1.7. As example, a MS of 1 may represent one ethylene oxide unit per monosaccharide unit.

The Degree of Substitution (DS) of cationic guars, that is the average number of hydroxyl groups that have been substituted by a cationic group per monosaccharide unit, may be comprised between 0.005 and 3, preferably between 0.01 and 2. DS may notably represent the number of the carboxymethyl groups per monosaccharide unit. DS may notably be determined by titration.

The Charge Density (CD) of cationic guars may be comprised between 0.1 and 2 meq/g, preferably between 0.4 and 1 meq/g. The charge density refers to the ratio of the number of positive charges on a monomeric unit of which a polymer is comprised to the molecular weight of said monomeric unit. The charge density multiplied by the polymer molecular weight determines the number of positively charged sites on a given polymer chain.

The cationic guar may have an average Molecular Weight (Mw) of between about 100,000 daltons and 3,500,000 daltons, preferably between about 500,000 daltons and 3,500,000 daltons.

The seed coating composition may also comprise a binder. The binder (or any of the layers) can be molasses, granulated sugar, alginates, karaya gum, jaguar gum, tragacanth gum, polysaccharide gum, mucilage, gelatin, polyvinyl acetates, polyvinyl acetate copolymers, polyvinyl alcohols, polyvinyl alcohol copolymers, styrene acrylate polymers, styrene butadiene polymers, celluloses (including ethylcelluloses and methylcelluloses, hydroxypropylcelluloses, hydroxymethyl celluloses, hydroxymethylpropyl-celluloses), polyvinylpyrolidones, dextrins, malto-dextrins, polysaccharides, fats, oils, proteins, gum arabics, shellacs, vinylidene chloride, vinylidene chloride copolymers, calcium lignosulfonates, acrylic copolymers, starches, derivatized starches, polyvinylacrylates, zeins, carboxymethylcellulose, chitosan, polyethylene oxide, acrylimide polymers and copolymers, polyhydroxyethyl acrylate, methylacrylimide monomers, alginate, ethylcellulose, polychloroprene, syrups or any combination thereof.

In another embodiment, the seed coating composition contains at least one active ingredient. The active ingredient can be one or more herbicides, plant growth regulators, crop dessicants, fungicides, bacteriocides, bacteriostats, insecticides, insect repellants, triazine herbicides, sulfonylurea herbicides, uracils, urea herbicides, acetanilide herbicides, organophosphonate herbicides, glyphosate salts, glyphosate esters, nitrilo oxime fungicides, imidazole fungicides, triazole fungicides, sulfenamide fungicides, dithio-carbamate fungicides, chloronated aromatic, dichloro aniline fungicides, carbamate insecticides, organo thiophosphate insecticides; perchlorinated organic insecticides, methoxychlor, miticides, propynyl sulfite, triazapentadiene miticides, chlorinated aromatic miticides, tetradifan, dinitrophenol miticides, binapacryl, or any mixture thereof.

According to an embodiment of the present invention, the seeding composition comprises at least a cationic guar and a plant biostimulant. Plant biostimulants are usually components other than fertilizers that affect plant growth and/or metabolism upon foliar application or when added to soil. Plant biostimulants generally fall within one of three categories: hormone-containing products, amino acid-containing products and humic acid-containing products. Plant biostimulants are used to treat crops in a commercial setting in view of their ability to, for example, increase growth rates, decrease pest plant growth, increase stress tolerance, increase photosynthetic rate, and increase disease tolerance. Plant biostimulants are generally believed to operate by up-regulating or down-regulating plant hormones.

The seed coating composition may also contain pigments, adjuvants, surfactants, and/or fertilizers.

The seed coating composition may be a liquid or solid composition, notably a powder. Suitable coating techniques may be utilized to coat the seeds or agglomeration of seed of the seed coating compositions described herein. Equipment that may be utilized for coating can include but are not limited to drum coaters, rotary coaters, tumbling drums, fluidized beds and spouted beds, but any suitable equipment or technique may be employed. The seeds may be coated via a batch or continuous coating process.

The seeds can be separated prior to coating which, in one embodiment, utilizes mechanical means such as a sieve. The separated seeds can then be introduced into a coating machine having a seed reservoir. In one embodiment, the seeds in the mixing bowl are combined with one or more of the coatings described herein and adhered with a binder or adhesive.

In one embodiment of the process, one or more layers can be added to coat the seed or agglomeration. Outer layers can be introduced sequentially to the rotating drum.

In another embodiment, agglomerators or agglomerator devices may also be utilized. Coating is performed within a rotary coater by placing seeds within a rotating chamber, which pushes the seeds against the inside wall of the chamber. Centrifugal forces and mixing bars placed inside the coater allow the seed to rotate and mix with a coating layer. Binder or other coating materials can be pumped into the proximate center of the coater onto an atomizer disk that rotates along with the coating chamber. Upon hitting the atomizer disk, liquid adhesive is then directed outward in small drops onto the seed.

In one embodiment, seed coating techniques include, for example, seed in a rotating pan or drum. Seed is then mist with water or other liquid and then gradually a fine inert powder, e.g., diatomaceous earth, is added to the coating pan. Each misted seed becomes the center of a mass of powder, layers, or coatings that gradually increases in size. The mass is then rounded and smoothed by the tumbling action in the pan, similar to pebbles on the beach. The coating layers are compacted by compression from the weight of material in the pan. Binders often are incorporated near the end of the coating process to harden the outer layer of the mass. Binders can also reduce the amount of dust produced by the finished product in handling, shipping and sowing. Screening techniques, such as frequent hand screening, are often times utilized to eliminate blanks or doubles, and to ensure uniform size. For example, tolerance for seed coating compositions described herein can be +/−1/64th inch (0.4 mm), which is the US seed trade standard for sizing, established long before coatings were introduced. For example, coated lettuce seed is sown most frequently with a belt planter through a 13/64 inch diameter round holes in the belt. This hole size requires that the seed coating compositions comprising lettuce seeds can be sized over a 7.5/64 inch screen and through an 8.5/64 inch screen.

In an another embodiment, the seed coating compositions and methods described herein comprises "in situ coating". In situ coating means, in one embodiment, where a raw or non-coated seed is implanted in a hole in the ground and immediately or soon thereafter a coating composition is sprayed or applied directly into the hole to surround or partially surround the seed. According to the invention the hole may notably be a hole, a cavity or a hollowed area. Typically, the application of the seed as well as application of the coating composition are performed mechanically, but is understood that either or both of the referenced applications can be performed manually as well.

The invention will now be further illustrated by the following non limiting examples.

EXPERIMENTAL PART

In these experiments, guar based additives are used accordingly:

| | Guar | DS | Mw | CD |
|---|---|---|---|---|
| C1 | Non cationic guar | 0 | 2M | 0 |
| C2 | Non cationic hydroxypropylether guar | 0 | 2M | 0 |
| 1 | Hydroxypropyl guar hydroxypropyltrimonium chloride | 0.10 | 1.5M | 0.5 |
| 2 | Guar Hydroxypropyltrimonium Chloride | 0.10-0.13 | 2M | 0.6-0.7 |
| 3 | Guar Hydroxypropyltrimonium Chloride | 0.17-0.20 | 2M | 0.9-1.1 |

Example 1: Growth Enhancement on Chinese Cabbage

Spraying with 0.4 wt % of aqueous solution of additives on the surface of *Brassica chinensis* seed (Chinese Cabbage), to obtain a weight ratio additive/seed of 0.2%. 50 g of soil in each pot are used; this soil coming from ShanXi province and belongs to clayey soil. The germination test is carried out under watering conditions of 10 mL water each 2 days, with a temperature is 25° C.

| Additive | Germination rate (3 days) | Germination rate (5 days) | Height (5 days) |
|---|---|---|---|
| C1/None - control soil | 34% | 80% | 2.4 cm |
| 1/Guar 1 | 56% | 90% | 2.9 cm |

Germination rate means the number of plant emerging out of soil in comparison with the number of all introduced in the soil. Height is the medium height of all plants in a set.

It appears then not only the germination rate of the plant is increased in comparison with a blank treatment, but also the kinetic of the growth. Consequently, the germination occurs early and then let more time for the plant to grow up.

Example 2: Growth Enhancement on Wheat Seeds

Spraying with 1 wt % of aqueous solution of additives on the surface of Wheat seeds, to obtain a weight ratio additive/seed of 0.4%. 900 g of soil in each pot are used; this soil coming from ShanXi province and belongs to clayey soil.

The germination test is carried out under watering conditions of 10 mL water each 2 days, with a temperature is 25° C.

| Additive | Germination rate (4 days) | Germination rate (6 days) |
|---|---|---|
| C1/None - control soil | 68% | 89% |
| 1/Guar 1 | 81% | 94% |

It appears then that the seed treatment of the present invention permits to increase the germination rate but also to boost the germination early in comparison with seeds that do not provide a coating treatment.

Example 3: Growth Enhancement on Wheat Seeds with Pesticide Treatment

Spraying an aqueous solution comprising 0.4 wt % of Guar 1 and 0.4 wt % of tebuconazol additives on the surface of Wheat seeds, to obtain a weight ratio Guar 1/seed of 0.2% and tebuconazol/seed of 0.1%. 900 g of soil in each pot are used; this soil coming from ShanXi province and belongs to clayey soil. The germination test is carried out under watering conditions of 25 ml water each 2 days, with a temperature is 25° C.

| Additive | Germination rate (36 days) | Height (36 days) |
|---|---|---|
| C1/None - control soil | 91% | 13.6 cm |
| C2/tebucanozol | 47% | 4.6 cm |
| 1/tebucanozol and Guar 1 | 54% | 6.9 cm |

It appears then not only the germination rate of the plant is increased in comparison with a blank treatment, but also the kinetic of the growth inducing an enhancement of the plant's height. It also appears that the presence of the cationic guar permit to partially decrease the detrimental effect of fungicide on germination rate and growth of the plant.

Example 4: Cationic Guars on Growth Enhancement of Wheat Seeds

Spraying 0.4% additive solution on seed while stirring it. The additive/seed weight ratio is 0.2%. Drying the seed at room temperature for 5 days. Then planted them in ShanXi province's soil with 1 mm depth. The germination test is carried out under watering conditions of 2 mm/day, with a temperature of 25° C. for the night and 32° C. for the day.

| Additive | Germination rate (4 days) | Germination rate (7 days) | Height (cm) 7 day |
|---|---|---|---|
| C1/None - control soil | 60% | 75% | 8.6 cm |
| C2/Guar C1 | 65% | 85% | 9.1 cm |
| C3/Guar C2 | 60% | 75% | 9.7 cm |
| 1/Guar 1 | 85% | 95% | 13.7 cm |
| 2/Guar 2 | 80% | 95% | 16 cm |
| 3/Guar 3 | 80% | 100% | 11.9 cm |

It appears then not only the germination rate of the plant is increased in comparison with a blank treatment, but also the kinetic of the growth inducing an enhancement of the plant's height.

Example 5: Cationic Guars on Field Results

Soybean seed was coated by powder additive with the help of binder. The additive/seed weight ratio is 0.2%. There were planted in field of d'Averdon in France.

Trials with irrigation of 30 mm/time after an entire harvesting season. In addition to natural rainfall, each time the plant exhibited symptoms of lack of water, an irrigation of 30 mm was made to provide a sufficient irrigation.

| Additive | Weight of 1000 grains | Average root length | Yield/plant |
|---|---|---|---|
| C1/None - control soil | 509.1 g | 17 cm | 105 g |
| 1/Guar 1 | 562.6 g | 20.4 cm | 134 g |

Trials with irrigation of 15 mm/time after an entire harvesting season. In addition to natural rainfall, each time the plant exhibited symptoms of lack of water, an irrigation of 15 mm was made to provide an insufficient irrigation

| Additive | Weight of 1000 grains | Average root length | Yield/plant |
|---|---|---|---|
| C1/None - control soil | 457.4 g | 16.4 cm | 83 g |
| 1/Guar 1 | 560.2 g | 26.4 cm | 115 g |

It appears then not only the germination rate of the plant is increased in comparison with a blank treatment, but also the number of pods, the weight of grains and size, the length of roots and the general yield of produced plants.

What is claimed is:

1. A method to increase the growth of a plant compared to a method not comprising coating a seed of said plant with a cationic guar, the method comprising coating a seed of said plant with a composition comprising at least a cationic guar, wherein the cationic guar comprises: (i) a Degree of Substitution comprised between 0.005 and 3, (ii) a charge density between 0.1 and 2 meq/g, or both (i) and (ii).

2. The method according to claim 1 comprising:
   a) coating the seed of said plant with the composition comprising the at least said cationic guar; and
   b) applying the coated seed onto or in soil.

3. The method according to claim 1 comprising:
   a) implanting a raw or non-coated seed in a hole in soil; and
   b) applying the composition comprising the at least said cationic guar into the hole to surround or partially surround the seed, thereby coating the seed.

4. The method according to claim 1, wherein the seed is selected from the group consisting of: corn, wheat, sorghum, soybean, tomato, cauliflower, radish, cabbage, canola, lettuce, rye grass, grass, rice, cotton, and sunflower.

5. The method according to claim 1, wherein cationic guars are obtained by a process comprising a cationic etherifying agent.

6. The method according to claim 1, wherein cationic guars are obtained by a process comprising quaternary ammonium salts as cationic etherifying agent.

7. The method according to claim 6, wherein the quaternary ammonium salts are selected from the group consisting of: 3-chloro-2-hydroxypropyl trimethyl ammonium chloride, 2,3-epoxypropyl trimethyl ammonium chloride, and diallyldimethyl ammonium chloride.

8. The method according to claim 1, wherein cationic guars are selected from the group consisting of cationic hydroxyalkyl guars and cationic carboxylalkyl guars.

9. The method according to claim 1, wherein cationic guars are guars hydroxypropyltrimonium chloride.

10. The method according to claim 1, wherein cationic guars have an average Molecular Weight of between about 100,000 daltons and 3,500,000 daltons.

11. The method according to claim 1, wherein the composition further comprises a binder.

12. The method according to claim 1, wherein the composition further comprises an active ingredient.

13. The method according to claim 1, wherein the composition further comprises a plant biostimulant.

14. The method according to claim 8, wherein the cationic hydroxyalkyl guars comprise cationic hydroxyethyl guar (HE guar), cationic hydroxypropyl guar (HP guar), or cationic hydroxybutyl guar (HB guar).

15. The method according to claim 8, wherein the cationic carboxylalkyl guars comprise cationic carboxymethyl guar (CM guar), cationic alkylcarboxy guars, or carboxymethylhydroxypropyl guar (CMHP guar).

16. The method according to claim 15, wherein cationic alkylcarboxy guars comprise cationic carboxylpropyl guar (CP guar) or cationic carboxybutyl guar (CB guar).

17. The method according to claim 1, wherein the method is compared to a method comprising coating a seed of said plant with a non-cationic guar.

* * * * *